(12) United States Patent
Hutten

(10) Patent No.: US 6,571,120 B2
(45) Date of Patent: May 27, 2003

(54) APPARATUS FOR IDENTIFYING THE CIRCULATORY EFFECTS OF EXTRASYSTOLES

(75) Inventor: Helmut Hutten, Graz (AT)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 173 days.

(21) Appl. No.: 09/737,843

(22) Filed: Dec. 15, 2000

(65) Prior Publication Data

US 2002/0022784 A1 Feb. 21, 2002

(30) Foreign Application Priority Data

Dec. 17, 1999 (DE) .......................................... 199 63 246

(51) Int. Cl.$^7$ ................................................. A61B 5/04
(52) U.S. Cl. ....................... 600/515; 600/508; 600/509; 600/513
(58) Field of Search ................................ 600/508, 509, 600/513, 515

(56) References Cited

U.S. PATENT DOCUMENTS

| | | |
|---|---|---|
| 3,524,442 A | 8/1970 | Horth |
| 4,018,219 A | 4/1977 | Hojaiban |
| 4,023,564 A | 5/1977 | Valiquette |

(List continued on next page.)

FOREIGN PATENT DOCUMENTS

| | | |
|---|---|---|
| DE | 2 304 173 | 8/1974 |
| DE | 197 49 393 A1 | 5/1999 |
| JP | 07132118 A | 5/1995 |

OTHER PUBLICATIONS

Meyer–Waarden, K. and N. Thompson, "An arrhythmia–anomalous best monitoring system," Biomedizinische Technik, Fachverlaf Schiele & Sohn GmbH (Berlin, Germany), vol. 18 (No. 6), p. 226–229, (Dec. 26, 1973).

Hsia, P–W, "Computer Arrhythmia Analysis in an Exercise System," 38th ACEMB, p. 65, (Sep. 3, 1985).

Primary Examiner—David J. Walczak
Assistant Examiner—Amanda Flynn
(74) Attorney, Agent, or Firm—Hahn Loeser + Parks LLP; Stephen L. Grant

(57) ABSTRACT

A cardiological device having a sensor, adapted to pick up at least one cardiac signal, and a signal processor including a first detector connected to the sensor, adapted to detect an individual signal or a feature parameter of the cardiac signal, wherein the signal processor further includes an averager connected to the first detector, for forming an average over a plurality of values of the feature parameter or over a plurality of individual signals, a second detector connected to the sensor, adapted to detect cardiological events, in particular extrasystoles, and a first comparator that is connected to the second detector, the averager and the first detector and which are adapted to determine a deviation of a feature parameter or individual signal ascertained in immediate time relationship with an event such as an extrasystole, from the corresponding average.

22 Claims, 1 Drawing Sheet

U.S. PATENT DOCUMENTS

| | | | |
|---|---|---|---|
| 4,066,069 A | 1/1978 | Dolch | |
| 4,357,944 A | 11/1982 | Mauser | |
| 4,499,904 A | 2/1985 | Sidorenko | |
| 4,510,944 A | 4/1985 | Porges | |
| 4,679,144 A | 7/1987 | Cox | |
| 4,862,361 A | 8/1989 | Gordon | |
| 4,893,632 A | 1/1990 | Armington | |
| 4,957,115 A | 9/1990 | Selker | |
| 4,964,410 A | 10/1990 | Leahey | |
| 5,012,411 A | 4/1991 | Policastro | |
| 5,113,869 A | 5/1992 | Nappholz | |
| 5,181,519 A * | 1/1993 | Bible | 600/515 |
| 5,187,657 A | 2/1993 | Forbes | |
| 5,201,321 A | 4/1993 | Fulton | |
| 5,265,617 A | 11/1993 | Verrier | |
| 5,277,189 A | 1/1994 | Jacobs | |
| 5,291,400 A | 3/1994 | Gilham | |
| 5,313,953 A | 5/1994 | Yomtov | |
| 5,355,891 A | 10/1994 | Wateridge | |
| 5,388,578 A | 2/1995 | Yomtov | |
| 5,411,031 A | 5/1995 | Yomtov | |
| 5,419,338 A | 5/1995 | Sarma | |
| 5,437,285 A * | 8/1995 | Verrier et al. | 128/925 |
| 5,560,370 A | 10/1996 | Verrier | |
| 5,570,696 A | 11/1996 | Arnold | |
| 5,704,365 A | 1/1998 | Albrecht | |
| 5,713,367 A | 2/1998 | Arnold | |
| 5,718,235 A | 2/1998 | Golosarky | |
| 5,724,984 A | 3/1998 | Arnold | |
| 5,791,944 A | 8/1998 | Grant | |
| 5,827,195 A | 10/1998 | Lander | |
| 5,842,997 A | 12/1998 | Verrier | |
| 5,853,364 A | 12/1998 | Baker | |
| 5,891,044 A | 4/1999 | Golosarky | |
| 5,908,393 A | 6/1999 | Albrecht | |
| 5,921,940 A | 7/1999 | Verrier | |
| 5,935,082 A | 8/1999 | Albrecht | |
| 6,052,616 A * | 4/2000 | Bonnet et al. | 600/515 |
| 6,304,773 B1 * | 10/2001 | Taylor et al. | 600/515 |

* cited by examiner

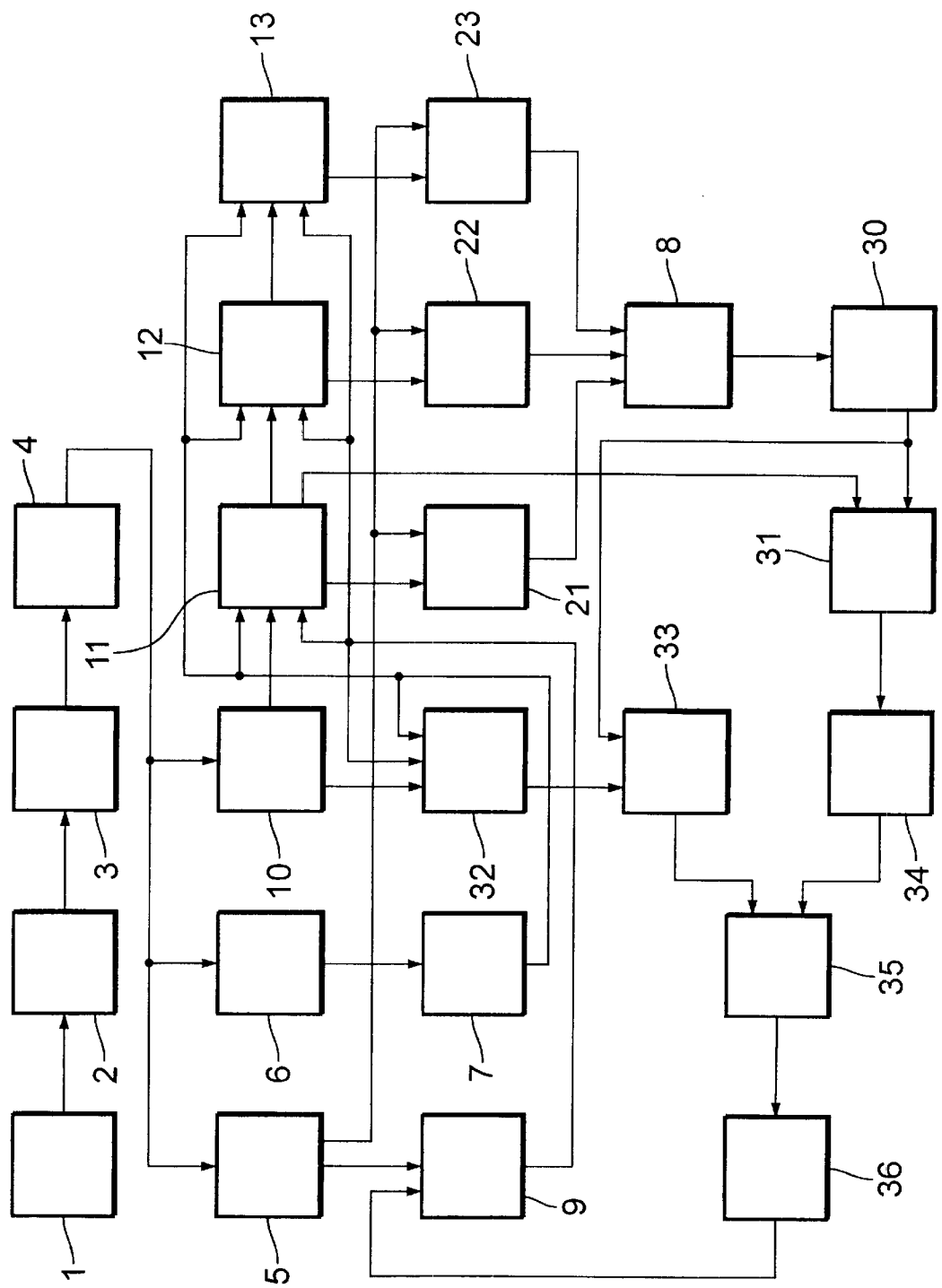

APPARATUS FOR IDENTIFYING THE CIRCULATORY EFFECTS OF EXTRASYSTOLES

The invention concerns a cardiological device having a sensor, adapted to pick up at least one cardiac signal, and signal processing means including first detection means connected to the sensor, adapted to detect an individual signal or a feature parameter of the cardiac signal.

BACKGROUND OF THE ART

The state of the art discloses devices having at least one sensor in order to obtain conclusions about the activity of the heart, from the electrophysiological measurement signal which is obtained with the sensor.

The previous devices are based on the notion that the occurrence of normal inherent excitation of the heart can be viewed as a direct and time-related reference to the functional capability of the heart as a mechanical pump for maintaining the stability of circulation. Extrasystoles are heart actions which do not occur in the normal rhythm of the cardiac activity. Depending on the location of excitation formation, they are subdivided into supraventricular or atrial extrasystoles and ventricular extrasystoles and are considered from the point of view of the frequency with which they occur. Occurrence in large numbers permits diagnostic conclusions to be drawn. Modern electrical cardiac pacemakers have devices for recognizing or identifying extrasystoles in order to take them into account in terms of the regular substitute function in respect of heart stimulation, appropriate to the task involved.

The known devices cannot implement more extensive investigation of the action which cardiological events such as extrasystoles have on the circulation and the behavior thereof immediately after they have occurred.

The object of the present invention is to provide a device which is capable of detecting the effect of cardiophysiological events such as extrasystoles or already indicating such events before they occur. In particular, the object of the invention is to provide a device which is suitable for detecting the effect of extrasystoles on the circulatory system including the heart and on the activity of the physiological systems controlling the circulatory system, and supplying more extensive information which can be used for diagnosis, for risk monitoring, for supporting therapy implementation and for improving items of electrical equipment, in particular electrical pacemakers.

SUMMARY OF THE INVENTION

In accordance with the invention, that object is attained by a device of the kind set forth in the opening part of this specification, the signal processing means of which additionally include:
  averaging means connected to the first detection means, adapted to form an average value over a plurality of values of the feature parameter or over a plurality of individual signals,
  second detection means connected to the sensor, adapted to detect cardiological events, in particular extrasystoles, and
  first comparison means which are connected to the second detection means, the averaging means and the first detection means and which are adapted to ascertain a deviation of at least one feature parameter or individual signal ascertained in the immediate time relationship with an event such as extrasystole from the corresponding average value.

The signal processing means also preferably additionally include second comparison means which are connected to the first comparison means and which are adapted to compare the deviation to a limit value, and signal means which are connected to the second comparison means and which are adapted to output a signal if the difference exceeds the limit value.

Preferably, that individual signal or that or those feature parameter or parameters directly following the event are used as the individual signal or signals in immediate time relationship with the event or as the feature parameter in immediate time relationship with the event.

Herein the term "cardiac signal" or "individual signal" are used in particular to denote a signal portion for example of an ECG signal, as occurs between two periodically recurring signal features, for example mutually corresponding zero-passages. An ECG signal in that sense comprises a train of individual signals which are delimited from each other by periodically recurring signal features.

The detection and storage of such signal portions or individual signals and also the formation of average values over a plurality of signal portions on the basis of predetermined time evaluation functions is already described in DE 199 38 376 to the present inventor, which is not a prior publication. The methods and means provided therein are also used in relation to the device described herein.

The invention involves the realization that, when recognizing or identifying the action of extrasystoles on the circulation and its performance and behavior, it is also necessary to observe those relationships which extend beyond an immediate association with the mechanical output of the heart. In particular, the invention takes account of the established realization that individual particularities such as the shape and size of the heart, the location of origin of the electrophysiological excitation of the heart, which is linked to extrasystoles, and pathophysiological changes in the circulatory system, can have an effect on the configuration of the measurement signal.

The invention is further based on the realization that signals which occur in immediate succession in a biological system never involve precisely the same fine signal structure but certain deviations can occur, the causes of which do not exclusively have to be related to the occurrence of extrasystoles.

Extrasystoles are heart excitations which occur earlier than is to be expected in the normal rhythm of the heart, having regard to other causes such as for example respiration or fluctuations in the activity of the autonomous nervous system. The immediate effect of extrasystoles can be diverse. A ventricular extrasystole can occur so early in the course of the normal cardiac cycle that the ventricle is only incompletely filled due to the atrium contraction which has not yet concluded at that time. Depending on the location at which the ventricular extrasystole is produced, it is also possible for the time-coordinated course of the ventricular contraction to be influenced. Many situations involve a more or less reduced beat volume and thus, as a further consequence, give rise to altered state parameters in the cardiovascular system which are established by existing physiological sensors, for example the pressor receptors in the aortic arch and in the carotid sinus and result in reactions on the behavior of the cardiovascular system. Atrial extrasystoles can also have an effect on the circulation by virtue of the fact that they occur prematurely in comparison with the normal rhythm of the heart, and because the ventricle is not completely filled, as a result. In general, atrial extrasystoles are distinguished in that the subsequent pause up to the next normal systole (the so-called post-extrasystolic pause) is longer than the pause which occurs in the normal rhythm of the heart. As a consequence of the prolonged pause, filling of the ventricle and thus the beat volume after an extrasystole can rather become somewhat greater, but at the same time the longer pause means that the situation can involve greater emptying of the vessel portions which are immediately downstream of the heart, with effects on the intravasal pressure which obtains there. In addition, there can be effects on different hormone systems, as a consequence of fluctuations in terms of circulatory effect. In addition, there is the action of the Frank Starling mechanism which describes a relationship, founded in the properties of the cardiac muscle, between filling of the heart and the beat volume. The various effects caused by extrasystoles are distinguished by different time constants which are reflected in the transitional characteristics in respect of time of the cardiovascular system until the original state is attained.

When matters are considered from a technical aspect, extrasystoles which have an effect on the circulation represent short-term disturbances in a system with multiple regulation. Most of the sub-systems which are activated by the disturbance have a compensatory action in the sense of restoring the initial condition.

The signals which are used to identify the effect on circulation of extrasystoles are electrical signals which are obtained in known manner with a sensor which is conductively connected to a device suitable for subjecting those signals to pre-processing and further processing. Pre-processing, for example amplification and frequency-determining filtering to remove those signal components which are not relevant in respect of information in terms of identifying the circulatory effectiveness can be effected in a manner corresponding to the state of the art. Some of the implantable pacemakers with sensing channel, which correspond to the state of the art, are capable of implementing such pre-processing. Pre-processing can be effected in analog or digital form.

The invention is based on a device which makes it possible to extract from a sequence of electrophysiological signals which are produced by heart excitations immediately after one or more extrasystoles, after suitable pre-processing, those feature parameters which permit assessment of the influence on the circulatory behavior, caused by extrasystoles. The feature extraction operation is advantageously implemented using digital processing, but basically it can also be effected in an analog or hybrid analog-digital processing procedure.

In accordance with the invention, the object of the invention is attained by a device which is provided with the capability of forming averages from the individual signals which occur in succession in respect of time. The averaging operation can be effected for the entire configuration of the individual signals, insofar as that is relevant in terms of assessing the circulatory behavior, or for certain features which are obtained from the individual signals and which are relevant in terms of assessing the circulatory behavior. The features obtained from the individual signals may be one feature or a plurality of features.

The averaging operation and the dispersion value-formation operation which is based thereon require for each individual signal a suitable time reference which is characteristic in respect of the feature parameter or signal configuration being considered. Preferably used for that purpose are the first signal passage through the line of the electrical zero signal, which occurs in connection with ventricle depolarization, or the maximum which occurs in connection with ventricle depolarization. Devices for determining the characteristic time reference point for each individual signal per se are known from the state of the art.

The operation of ascertaining the average can be based on a time assessment function. The averaging operation provides for adequately taking account of individual particularities. In addition, by virtue of the time assessment function, the device permits continual adaptation to changes in the signal configuration, which are caused by influences other than extrasystoles.

The device also enjoys the capability of forming a dispersion value from the deviation in the individual signals or the features obtained therefrom, from the average. That dispersion value is a statistical measurement in respect of the deviation of the individual signals or the features obtained therefrom from the average as a result of the physiological influencing factors to which extrasystoles do not belong.

Extrasystoles and a subsequent number of individual signals which are set forth in the claim of the invention in accordance with the state of the art are not taken into consideration either when forming the average or when calculating the dispersion value. As the operation of ascertaining the average and the dispersion value is effected continuously with the exception of the intervals characterized by the occurrence of extrasystoles, the requirement which is essential in accordance with the claim of the invention for time adaptation to varying circumstances which have effects on the fine signal structure but which are not related to the circulatory effects triggered by extrasystoles is met.

Each individual signal occurring in the interval following one or more extrasystoles is compared to the average which is stored up to the occurrence of the extrasystoles. In the case of stored signal configurations, that comparison can preferably be implemented by procedures such as cross-correlation, in the case of stored feature parameters by ascertaining the difference. The methods and devices to be used for that purpose are in accordance with the state of the art. This situation involves ascertaining a value which in simple quantitative fashion describes the deviation of the respective individual signal or the feature parameter extracted therefrom from the stored average.

The result is a sequence of positive and negative numbers which describes the deviation of the individual signals occurring after one or more extrasystoles or the feature parameter extracted therefrom, from the corresponding average, in terms of their time succession. That illustrates the effects caused by the one or more extrasystoles on the cardiovascular system in terms of their variation in respect of time, until the initial condition is restored.

More extensive assessment of the sequence of numbers ascertained in that fashion can be effected in different ways, for example by an assessing comparison with a number sequence stored in a look-up table or by approximation of the sequence of numbers to higher-order functions.

More extensive assessment and conversion of the result obtained thereby are not subject-matter of the invention insofar as the diagnostic knowledge or therapeutic conclusions to be drawn therefrom presuppose use of the device according to the invention in relation to a relatively large number of patients.

The invention thus involves in particular a device for identification of the circulatory effect caused by extrasystoles, wherein the device ascertains feature parameters which characteristic in respect of given circulation states, on the basis of continuous formation of averages with a time assessment function which can be set as desired, compares them to the individual signals occurring after one or more extrasystoles, and uses the deviation from a limit value on the basis of the dispersion value which is also continuously ascertained by the device according to the invention, as a decision criterion in respect of a circulatory effect.

Advantageous configurations of this device provide that:

the feature parameter used for identifying the circulatory effect as a consequence of one or more extrasystoles is the time interval between two immediately successive heart excitations, ascertained from the moments in time of the similar zero-passage of the electrophysiological signal detected with the sensor (1);

the feature parameter used for identifying the circulatory effect as a consequence of one or more extrasystoles is the time interval between two immediately successive heart excitations, ascertained from the moments in time of the occurrence of a signal maximum of the electrophysiological signal detected with the sensor (1);

the feature parameter used for identifying the circulatory effect as a consequence of one or more extrasystoles is the maximum of the electrophysiological signal detected with the sensor (1);

the feature parameter used for identifying the circulatory effect as a consequence of one or more extrasystoles is the cross-correlation coefficient between the average signal and the individual signal which actually occurred;

a plurality of feature parameters are ascertained and used in summarizing assessment as a criterion for identification of the circulatory effect as a consequence of one or more extrasystoles;

the feature parameters for identifying the circulatory effect as a consequence of one or more extrasystoles are determined during an interval which is fixed by a time presetting;

the feature parameters for identifying the circulatory effect as a consequence of one or more extrasystoles are determined during an interval which is fixed by a number of normal heart excitations after the triggering extrasystole;

the feature parameters for identifying the circulatory effect as a consequence of one or more extrasystoles are determined during an interval which is fixed by a threshold value derived from the dispersion value;

the sensor (1) for detecting the electrophysiological signal of heart excitation can also perceive other functions such as stimulation of the heart;

the sensor (1) for detecting the electrophysiological signal of heart excitation comprises a plurality of components;

the device is implanted in a housing suitable therefore, entirely in the body of a human being;

the device is disposed jointly with an electrical pacemaker in a housing and is implanted entirely in the body of a human being; and the device is used to suitably adapt the stimulation frequency of an electrical pacemaker to the circulation demands of the patient.

As the signal configuration prior to one or more extrasystoles is also stored in the device according to the invention when ascertaining one or more extrasystoles, the device can also be slightly modified in such a way that feature parameters or individual signals recorded immediately prior to one or more extrasystoles are compared to the corresponding average values from previously recorded regular signal configurations in the manner described herein or in DE 199 38 376, and analyzed, in order to be able to output a corresponding signal before the occurrence of a (further) extrasystole.

BRIEF DESCRIPTION OF THE DRAWING

FIG. 1 shows the essential functional units and the operationally appropriate arrangement thereof, with which the classifying portion of the claim can be carried into effect. The numerals set forth in the text in relation to the functional units correspond to the numerals used in FIG. 1 to identify the functional units.

DETAILED DESCRIPTION OF THE INVENTION

The signal recorded with the sensor 1 as an expression of heart excitation is fed, after suitable pre-processing which in the present example is effected in analog form with an input amplifier 2 and a filter 3, to an analog-digital converter 4. The analog-digital conversion operation must be effected with a sufficiently high sampling rate and with adequate amplitude discretization so that no falsification or elimination is thereby effected in respect of those signal components which are essential for identification of the effects on the cardiovascular system, which are caused by one or more extrasystoles.

The digitized signal obtained that way is fed to a plurality of functional units:

1. a device 5 for identifying that there are one or more extrasystoles and the class to which they are to be allocated;
2. a device 6 for identifying the characteristic time reference point in each individual signal for the averaging and dispersion value formation operation;
3. a first memory 10 whose capacity must be sufficient to receive each individual signal with the time and amplitude discretization required for the task to be performed in accordance with the invention.

Arranged downstream of the memory 10 are N further memories 11, 12 . . . 1N of a similar structure, the memory capacity of which must correspond to the first memory 10. The number N of the similarly designed memories arranged in that way can be of any magnitude but must be at least equal to 2.

With the occurrence of an individual signal, the content of the first memory 10 is transferred into the immediately following memory 11 whose content is transferred into the immediately following memory 12 and so forth. It is only the content of the last memory 1N that is not transferred but lost. Transfer of the content of each memory into the subsequent memory is effected in a procedure which is ordered and coordinated by a clock generator 7 in such a way that the elements of the various individual signals, which correspond in relation to the characteristic time reference point, are in corresponding memory elements of each memory.

For that purpose the clock generator is activated by a control signal of the device for identifying the characteristic time reference point as indicated at 6.

The signal components which correspond to each other and which are contained in the successively arranged memories 11, 12 . . . 1N are fed by way of assessment devices 21, 22 . . . 2N to an adding device 8 when the next individual signal transferred into the memory 10 is not an extrasystole, which is established by the device 5 for identifying extrasystoles or falls into the fixed interval following the extrasystole. In that respect each of the assessment devices is connected in the same manner to one of the memories, for example the second memory 11 to the assessment device 21, the third memory 12 to the assessment device 22 and so forth. Overall therefore there are as many assessment devices as there are memories, with the exception of the first memory 10. It will be noted that each assessment device can be provided with its own assessment factor of between 1 and 0 with a suitable subdivision. In that way the content of each memory 11, 12 . . . 1N can be weighted multiplicatively with an adjustable assessment factor before it is fed to the adding device 8. Connected on the output side of the adding device 8 is a further memory 30 which is of the same design configuration as the memories 11 , 12 . . . 1N. Therefore, after the addition operation has been implemented, the content of that memory 30 corresponds to a signal which represents the average of the signals contained in the memories 11, 12 . . . 1N, that average being freshly formed with the occurrence of each individual signal and ascertained on the basis of a weighting function which can be set as desired and the characteristic time reference value.

If the device 5 for identifying extrasystoles establishes the occurrence of one or more extrasystoles, signal transfer in the memory arrangement 10, 11, 12 . . . 1N into the respective following memory is inhibited by way of the interval presetting device 9. The inhibition effect remains operative for the entire duration of each interval following the one or more extrasystoles, during which the circulatory effects caused by the one or more extrasystoles last. In that way, during that interval, the N normal systoles immediately preceding the one or more extrasystoles are present in the memories 11, 12, . . . 1N in an ordered sequence. The weighted average of the N normal systoles immediately preceding the one or more extrasystoles in the average value memory 30 thus remains unchanged during that interval.

As the individual signals which successively occur in a biological system are never identical, a dispersion value is additionally formed from the signals stored in the memories 11, 12 . . . 1N, in the dispersion value ascertaining device 31, by comparison of the individual signal contained in the memory 11 with the average value signal contained in the average value memory 30. This dispersion value represents a measurement in respect of the normal or physiological dispersion width of the individual signals which correspond to normal excitation processes, around that average which is ascertained continuously and weightedly. Devices for ascertaining the dispersion value are known and correspond to the state of the art. Microprocessors are preferably used for that purpose.

During the duration of the interval, which duration is fixed by the device 9 and in which the contents of the memories 11, 12 . . . 1N remain unchanged, the content of the first memory 10 is transferred into the memory 32 in the same manner as in which outside that interval transfer from the first memory 10 into the subsequent memory 11 takes place. In that respect, the content which is contained in the memory 32 up to that moment in time is lost. Therefore, what is in the memory 32 in each case is the signal which occurred last and which falls in the interval triggered by the extrasystole.

The device 33 provides for quantitatively ascertaining the deviation of the content of the memory 32 from the content of the average value memory 30. Comparison of the two signals can relate both to the overall signal configuration and also to each feature which is characteristic in respect of the state of given circulatory parameters. Those features can involve time features, for example the occurrence of characteristic points in the signal configuration such as the first passage through the electrical zero line with beginning ventricle depolarization or the maximum which is to be found during depolarization, time differences, for example the duration of the positive signal configuration upon depolarization, or amplitude values, for example the magnitude of the maximum which is to be found during depolarization.

The deviation which is found in the device 33 for quantitatively ascertaining the deviation between the content of the average value memory 30 and the content of the memory 32 is related to the dispersion value which occurs in a situation involving normal cardiac activity. For that purpose, in the comparison circuit 35, the value of the deviation, which is ascertained in the device 33, is compared to a value which has been formed in the device 34 from the dispersion value ascertained by the dispersion value ascertaining device 31. A circulatory effect as a consequence of the one or more extrasystoles which occurred applies if the comparison circuit 35 detects a difference between those two values. The sequence of numbers produced by the device 35 is available for more extensive evaluation for diagnostic assessment, identification of risk development, therapy support or control of items of medical-engineering equipment.

As the absence of a difference indicating a circulatory effect can be caused by chance, for example in the case of an oscillating fluctuation at the zero-passage, the device 36 checks whether the zero condition is met at k successive heart excitations, in which respect k can be of any desired magnitude and must be at least equal to 2.

What is claimed is:

1. A cardiological device comprising:
   a sensor for picking up at least one cardiac signal, and
   a means for processing a signal including a first means for detecting an individual signal or a feature parameter of the cardiac signal connected to the sensor,
   wherein the signal processing means further comprises:
      means for averaging connected to the first detection means, for forming an average over a plurality of values of the feature parameter or over a plurality of individual signals,
      a second means for detecting cardiological events, connected to the sensor, and
      a first means for comparing and determining a deviation of a feature parameter or individual signal ascertained in immediate time relationship with at least one cordiological event such as an extrasystole or a sequence of extrasystoles, from the corresponding average, connected to the second detection means, the averaging means and the first detection means.

2. The device as set forth in claim 1 characterized by:
   a second comparison means connected to the first comparison means, for comparing the deviation to a limit value, and
   a signal means connected to the second comparison means, for outputting a signal when the difference exceeds the limit value.

3. The device as set forth in claim 1, further comprising a means for ascertaining a dispersion value for the feature parameter or parameters, connected to the first detection means.

4. The device as set forth in claim 3, further comprising a means for forming a limit value on the basis of the dispersion value, connected to the dispersion value ascertaining means.

5. The device as set forth in claim 1, further comprising a means for inhibiting that is connected to the second detection means and to the averaging means such that at least one individual signal occurring in immediate time relationship with a cardiological event such as an extrasystole or a corresponding feature parameter is not involved in the averaging operation.

6. The device as set forth in claim 1, wherein the first comparison means compares feature parameters or individual signals ascertained immediately after a cardiological event such as an extrasystole to the corresponding average.

7. The device as set forth in claim 1, wherein the averaging means continuously effects the averaging operation based on a time assessment function which can be set as desired.

8. The device as set forth in claim 3, wherein the first detection means determines the feature parameter or parameters respectively within a predeterminable interval.

9. The device as set forth in claim 8 characterized in that the first detection means is connected to the dispersion value ascertaining means such that the first detection means determines the interval by a threshold value derived from the dispersion value.

10. The device as set forth in claim 1, wherein the feature parameter or the feature parameters detected by the first detection means are: the heart rate, measured from one signal maximum to the next or from one zero-passage to the next zero-passage of the same kind, the signal maximum or the cross-correlation coefficient of successive individual signals or a combination of those feature parameters.

11. The device as set forth in claim 2, further comprising a means for ascertaining a dispersion value for the feature parameter or parameters, connected to the first detection means.

12. The device as set forth in claim 11, further comprising a means for forming a limit value on the basis of the dispersion value, connected to the dispersion value ascertaining means.

13. The device as set forth in claim 12, further comprising a means for inhibiting that is connected to the second detection means and to the averaging means such that at least one individual signal occurring in immediate time relationship with a cardiological event such as an extrasystole or a corresponding feature parameter is not involved in the averaging operation.

14. The device as set forth in claim 4, further comprising a means for inhibiting that is connected to the second detection means and to the averaging means such that at least one individual signal occurring in immediate time relationship with a cardiological event such as an extrasystole or a corresponding feature parameter is not involved in the averaging operation.

15. The device as set forth in claim 9, further comprising a means for inhibiting that is connected to the second detection means and to the averaging means such that at least one individual signal occurring in immediate time relationship with a cardiological event such as an extrasystole or a corresponding feature parameter is not involved in the averaging operation.

16. The device as set forth in claim 13, wherein the first comparison means compares feature parameters or individual signals ascertained immediately after a cardiological event such as an extrasystole to the corresponding average.

17. The device as set forth in claim 15, wherein the first comparison means compares feature parameters or individual signals ascertained immediately after a cardiological event such as an extrasystole to the corresponding average.

18. The device as set forth in claim 16, wherein the averaging means continuously effects the averaging operation based on a time assessment function which can be set as desired.

19. The device as set forth in claim 17, wherein the averaging means continuously effects the averaging operation based on a time assessment function which can be set as desired.

20. The device as set forth in claim 18, wherein the first detection means determines the feature parameter or parameters respectively within a predeterminable interval.

21. The device as set forth in claim 20 characterized in that the first detection means is connected to the dispersion value ascertaining means such that the first detection means determines the interval by a threshold value derived from the dispersion value.

22. The device as set forth in claim 21, wherein the feature parameter or the feature parameters detected by the first detection means are: the heart rate, measured from one signal maximum to the next or from one zero-passage to the next zero-passage of the same kind, the signal maximum or the cross-correlation coefficient of successive individual signals or a combination of those feature parameters.

* * * * *